(12) United States Patent
Krause et al.

(10) Patent No.: US 8,771,516 B2
(45) Date of Patent: Jul. 8, 2014

(54) MEMBRANES HAVING IMPROVED PERFORMANCE

(75) Inventors: Bernd Krause, Rangendingen (DE); Carina Zweigart, Schoemberg (DE); Heinrich Behr, Hechingen (DE)

(73) Assignee: Gambro Lundia AB, Lund (SE)

(*) Notice: Subject to any disclaimer, the term of this patent is extended or adjusted under 35 U.S.C. 154(b) by 423 days.

(21) Appl. No.: 13/320,699

(22) PCT Filed: May 19, 2010

(86) PCT No.: PCT/EP2010/056845
§ 371 (c)(1),
(2), (4) Date: Dec. 9, 2011

(87) PCT Pub. No.: WO2010/133613
PCT Pub. Date: Nov. 25, 2010

(65) Prior Publication Data
US 2012/0074064 A1 Mar. 29, 2012

(30) Foreign Application Priority Data
May 20, 2009 (EP) .................. 09006809

(51) Int. Cl.
*A61M 1/18* (2006.01)
*A61M 1/34* (2006.01)
*B01D 61/24* (2006.01)
*B01D 71/68* (2006.01)
*B01D 71/42* (2006.01)
*B01D 71/56* (2006.01)
*B01D 69/08* (2006.01)
*B29C 47/08* (2006.01)

(52) U.S. Cl.
CPC .............. *B01D 69/088* (2013.01); *B01D 71/56* (2013.01); *B01D 71/68* (2013.01)
USPC ................... 210/646; 210/321.6; 210/500.23; 210/651; 210/654; 264/176.1; 264/177.14; 264/177.18; 264/211.18; 604/4.01; 604/5.01; 604/6.04; 604/6.09; 604/28

(58) Field of Classification Search
CPC ........ B01D 71/56; B01D 71/68; B01D 63/02; B01D 63/021; B01D 69/08; B01D 2325/022; B01D 69/088; B01D 71/42; B01D 61/00; B29C 47/08
USPC ............... 210/321.6, 321.62, 321.79, 321.88, 210/488, 490, 500.23, 500.24, 506, 645, 210/646, 651, 654; 264/176.1, 177.14, 264/177.18, 211, 211.13–211.19; 604/4.01, 604/5.04, 6.04, 6.09, 28
See application file for complete search history.

(56) References Cited

U.S. PATENT DOCUMENTS 5,340,480 A 8/1994 Kawata et al.
5,843,743 A 12/1998 Hubbell et al.
(Continued)

FOREIGN PATENT DOCUMENTS

EP 0305687 3/1989
EP 0305787 3/1989
(Continued)

OTHER PUBLICATIONS

PCT International Search Report and Written Opinion completed for PCT/EP2010/056844 Aug. 30, 2010.
(Continued)

*Primary Examiner* — John Kim
(74) *Attorney, Agent, or Firm* — Barnes & Thornburg LLP

(57) ABSTRACT

Permselective asymmetric membranes suitable e.g. for hemodialysis, hemodiafiltration and hemofiltration of blood, and having improved performance, including improved sieving characteristics, providing enhanced removal of middle molecular weight substances, e.g. inflammatory mediators having a molecular weight between 20 and 40 kDa. The improved sieving characteristics are due to a narrow pore size distribution of the membranes created in the production process. Processes for the preparation of these membranes, devices comprising these membranes, and the use of these membranes in hemodialysis, hemodiafiltration and hemofiltration of blood, as well as in bioprocessing, plasma fractionation and the preparation of protein solutions.

15 Claims, 6 Drawing Sheets

(56) References Cited

U.S. PATENT DOCUMENTS

| | | | |
|---|---|---|---|
| 6,074,559 | A | 6/2000 | Hahmann et al. |
| 7,087,168 | B2 | 8/2006 | Oishi et al. |
| 2003/0155294 | A1 | 8/2003 | Heilmann et al. |
| 2004/0045897 | A1 | 3/2004 | Nakabayashi et al. |
| 2004/0167237 | A1* | 8/2004 | Kim et al. ............ 521/50 |
| 2005/0273031 | A1 | 12/2005 | Ueno et al. |
| 2008/0000828 | A1 | 1/2008 | Wechs et al. |
| 2010/0000942 | A1* | 1/2010 | Muller et al. ............ 210/636 |

FOREIGN PATENT DOCUMENTS

| | | |
|---|---|---|
| EP | 0844015 | 5/1998 |
| JP | 2003320229 | 11/2003 |
| JP | 2008093154 | 4/2008 |
| KR | 20050078748 | 8/2005 |
| KR | 20050094968 | 9/2005 |
| WO | WO01/60477 | 8/2001 |
| WO | WO2004/056459 | 7/2004 |
| WO | WO2008/041183 | 4/2008 |

OTHER PUBLICATIONS

PCT International Search Report and Written Opinion completed for PCT/EP2010/056845 Aug. 17, 2010.

Hasegawa, Takashi, et al., "Preparation and Performance of Protein-Adsorption-Resistant Asymmetric Porous Membrane Composed of Polysulfone/Phospholipid Polymer Blend", 2001, Biomaterials, No. 22, pp. 243-251.

Klein, E., et al., "Transport and Mechanical Properties of Hemodialysis Hollow Fibers", 1976, Journal of Membrane Science, No. 1, pp. 371-396.

Nagase, Yu, et al., "Preparations of Aromatic Daimine Monomers and Copolyamides Containing Phosphorylcholine Moiety and the Biocompatibility of Copolyamides", 2007, Polymer Journal, vol. 39, No. 7, pp. 712-721.

Ye, Sang Ho, et al., "In Situ Modification on Cellulose Acetate Hollow Fiber Membrane Modified With Phospholipid Polymer for Biomedical Application", 2005, Journal of Membrane Science, No. 249, pp. 133-141.

Zhou, Jing, et al., "Phosphorylcholine-Modified Poly(Ethylene-co-Vinyl Alcohol) Microporous Membranes With Improved Protein-Adsorption-Resistance Property", 2007, Journal of Membrane Science, No. 305, pp. 279-286.

Qin et al., "A high flux ultrafiltration membrane spun from PSU/PVP (K90)/DMF/1,2-propanediol", Journal of Membrane Science 211 (2003) 139-147.

* cited by examiner

MEMBRANES HAVING IMPROVED PERFORMANCE

CROSS REFERENCE TO RELATED APPLICATIONS

This application is the U.S. national phase of PCT/EP2010/056845 filed May 19, 2010. PCT/EP2010/056845 claims benefit under the Paris Convention to European patent application 09006809.9 filed May 20, 2009. The disclosures of EPA09006809.9 and PCT/EP2010/056845 are hereby incorporated herein by reference.

TECHNICAL FIELD

The present invention relates to permselective asymmetric membranes being suitable e.g. for hemodialysis, hemodiafiltration and hemofiltration of blood, and having improved performance, allowing for enhanced removal of middle molecular weight substances, e.g. inflammatory mediators having a molecular weight between 20 and 40 kDa. The improved sieving characteristics are due to a narrow pore size distribution of the membranes created in the production process. The invention also relates to processes for the preparation of said membranes, devices comprising said membranes, and the use of said membranes in hemodialysis, hemodiafiltration or hemofiltration of blood, as well as in bioprocessing, plasma fractionation and the preparation of protein solutions.

BACKGROUND OF THE INVENTION

EP 0 305 787 A1 discloses a permselective asymmetric membrane suitable for hemodialysis, hemodiafiltration and hemofiltration of blood, comprised of a hydrophobic first polymer, e.g. polyamide, a hydrophilic second polymer, e.g. polyvinylpyrrolidone, and suitable additives. The membrane has a three-layer structure, comprising a first layer in the form of dense, rather thin skin, responsible for the sieving properties, a second layer in the form of a sponge structure, having a high diffusive permeability and serving as a support for said first layer, and a third layer in the form of a finger structure, giving the membrane a mechanical stability.

WO 2004/056459 A1 discloses a permselective asymmetric membrane suitable for hemodialysis, comprising at least one hydrophobic polymer, e.g. polyethersulfone, and at least one hydrophilic polymer, e.g. polyvinylpyrrolidone. The outer surface of the hollow fiber membrane has pores in the range of 0.5 to 3 µm and the number of pores in the outer surface is in the range of 10,000 to 150,000 pores per $mm^2$.

While these membranes already show very good performance in hemodialysis and excellent biocompatibility, there is a desire to further improve their performance to enhance removal of middle molecular weight substances, e.g. inflammatory mediators having a molecular weight between 20 and 40 kDa. It has now been found that membranes with improved performance can be obtained by a particular production process which comprises a step of treating the membranes with a salt solution before drying them.

SUMMARY OF THE INVENTION

It is an object of the present invention to improve the performance of particular permselective asymmetric membranes suitable for, e.g., hemodialysis, hemodiafiltration and hemofiltration of blood, so that removal of middle molecular weight substances, e.g. inflammatory mediators having a molecular weight between 20 and 40 kDa, is enhanced.

According to one aspect of the invention, a permselective asymmetric membrane having improved performance is provided. The difference of the sieving coefficient of the membrane for ovalbumin (MW=44 kDa) in aqueous solution and the sieving coefficient of the membrane for albumin (MW=66 kDa) in aqueous solution is at least 50%. In a particular embodiment, the membrane comprises polyethersulfone and polyvinylpyrrolidone and, optionally, polyamide.

According to a further aspect, the invention relates to a process for preparing the permselective asymmetric membrane of the invention. In one embodiment of the process, a hollow fiber membrane is obtained by treating the membrane with a salt solution before drying it.

DETAILED DESCRIPTION

Figure 1:
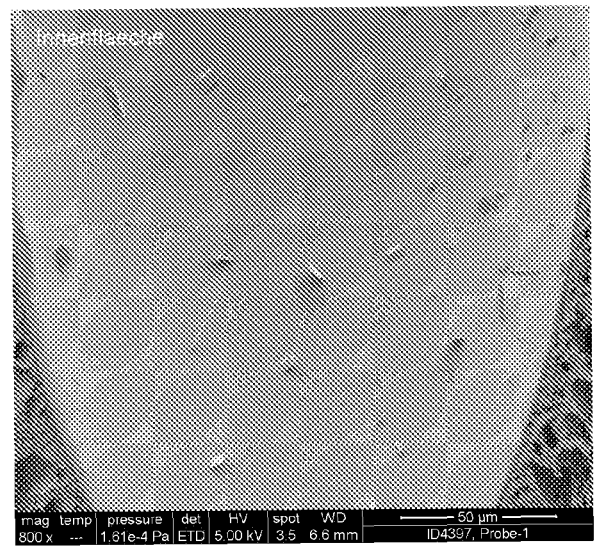
FIG. 1 presents scanning electron micrographs of a membrane of the invention with salt crystals in the pore entrances.
Figure 1:
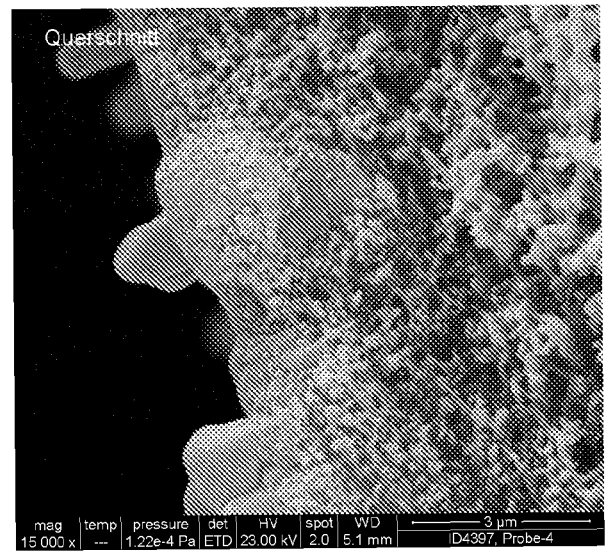

In one embodiment of the invention, the permselective asymmetric membrane is based on at least one hydrophobic polymer. Said at least one hydrophobic polymer is selected from the group consisting of polysulfones, polyethersulfones, polyamides and polyacrylonitriles. In one embodiment, said hydrophobic polymer is a polysulfone, a polyethersulfone (PES) or a polyarylethersulfone (PAES), optionally in combination with polyamide. In one embodiment, the membrane also comprises at least one hydrophilic polymer. In one embodiment, said at least one hydrophilic polymer comprises polyvinylpyrrolidone (PVP). In one embodiment, a polyvinylpyrrolidone which consists of a low molecular weight component having a molecular weight of below 100 kDa and a high molecular weight component having a molecular weight of 100 kDa or more, is used for preparing the membrane.

In one embodiment, the membrane of the present invention comprises 80-99 wt.-% of polyethersulfone and 1-20 wt.-% of polyvinylpyrrolidone (PVP).

An example of a suitable polyethersulfone is a polymer having the general formula —[O-Ph-$SO_2$-Ph-]$_n$—, a weight average molecular weight of about 60,000 to 65,000 Da, preferably 63,000 to 65,000 Da, and a Mw/Mn of about 1.5 to 1.8.

An example of a suitable PVP consisting of a high 100 kDa) and low (<100 kDa) molecular component comprises 10-45 weight-%, based on the total weight of PVP in the membrane, of a high molecular weight component, and 55-90 weight-%, based on the total weight of PVP in the membrane, of a low molecular weight component.

In one embodiment, the membrane of the invention is a hollow fiber membrane having a very specific four-layer structure.

The inner layer of the four-layer structure, i.e. the blood contacting layer and the inner surface of the hollow fiber membrane, is a separation layer in the form of a dense, rather thin layer having, in one embodiment, a thickness of less than 1 μm and a pore size in the nano-scale range. To achieve high selectivity, the pore channels with the responsible pore diameters are short, i.e. below 0.1 μm. The pore channel diameter has a low variation in size. The defined pore structure is achieved by selection of the composition of the polymer, the composition and condition of the precipitation media in the center fluid and by the condition and composition of the surrounding environment of the fiber leaving the spinning nozzle.

The next layer in the hollow fiber membrane is the second layer having the form of a sponge structure and, in one embodiment of the present invention, a thickness of about 1 to 15 μm, and serves as a support for said first layer.

Then, there is the third layer having the form of a finger structure. It provides for mechanical stability on the one hand; on the other hand it has, through the high void volume, a very low resistance of transport of molecules through the membrane. During the process, the voids are filled with water, and the water gives a lower resistance for diffusion and convection than a matrix with a sponge-filled structure having a lower void volume. Accordingly, the third layer gives the membrane mechanical stability and has, in one embodiment of the present invention, a thickness of 20 to 60 μm.

The fourth layer in this embodiment of the present invention is the outer layer, which is characterized by a homogeneous and open pore structure with a defined surface roughness. The openings of the pores are in the size range of 0.5-3 μm, further the number of pores on the outer surface is in the range of 10,000 to 150,000 pores per $mm^2$, for example in the range of 18,000 to 100,000 pores per $mm^2$, or even in the range of 20,000 to 100,000 pores per $mm^2$. In one embodiment, this fourth layer has a thickness of about 1 to 10 μm.

This four-layer design provides for a high selectivity, which means, a high potential to separate molecules, which are close in their size, for example, to separate albumin, which is to be retained, from a $\beta_2$-microglobulin and Factor D.

The membrane according to the present invention, due to its specific preparation and membrane characteristics as described before, is especially characterized by a high convective permeability Lp and a high diffusive permeability for small molecules, such as, for example, urea or chloride ($P_{Cl}$). The Lp is in the range of from $50 \cdot 10^{-4}$ to $600 \cdot 10^{-4}$ cm/bar·s, for example from 60 to $300 \cdot 10^{-4}$ cm/bar·s, or from 100 to $180 \cdot 10^{-4}$ cm/bar·s. The chloride permeability $P_{Cl}$ is in the range of from $13 \cdot 10^{-4}$ to $23 \cdot 10^{-4}$ cm/s, e.g. from $19 \cdot 10^{-4}$ to $22 \cdot 10^{-4}$ cm/s, or from $13 \cdot 10^{-4}$ to $16 \cdot 10^{-4}$ cm/s. The diffusive permeability can be determined according to E. Klein, F. Holland, A. Lebeouf, A. Donnaud, J. K. Smith, "Transport and Mechanical Properties of Hemodialysis Hollow Fibers", Journal of Membrane Science 1 (1976) 371-396, especially pages 375-379.

The membrane is further characterized by a high selectivity, i.e. a high removal rate for middle molecules. The difference of the sieving coefficient of the membrane of the invention for ovalbumin (MW=44 kDa) in aqueous solution and the sieving coefficient of the membrane for albumin (MW=66 kDa) in aqueous solution is at least 50%, for example at least 53%, or at least 56%, or even at least 59%. The sieving coefficients are determined using protein solutions in PBS buffer having a pH of 7.2 and maintained at a temperature of 37±1° C.

The membrane can be prepared by a solvent phase inversion spinning process, comprising the steps of
  a) dissolving at least one membrane-forming polymer in at least one solvent to form a polymer solution;
  b) extruding said polymer solution through an outer ring slit of a nozzle with two concentric openings;
  c) extruding a center fluid through the inner opening of the nozzle; and thereafter
  d) washing the membrane obtained and, drying said membrane and, optionally, sterilizing said membrane e.g. by treatment with steam, ethylene oxide or radiation;
wherein the membrane is treated with a salt solution before the drying step. In one embodiment, the salt solution is a sodium chloride solution.

Without wishing to be bound by theory, it is believed that the salt crystallizes in the pores of the membrane during the drying process, leading to a more open structure with uniform pore sizes. FIG. 1 presents scanning electron micrographs of a membrane of the invention. Salt crystals residing in the pore entrances of the selective layer, i.e. the inner surface can be seen. It is assumed that the salt crystals prevent pore shrinkage during the drying process and a membrane having more uniform pore diameters is obtained.

In one embodiment, the spinning solution for preparing a membrane according to the present invention comprises from 12 to 16 wt.-% of polyethersulfone as hydrophobic polymer and from 3 to 12 wt.-%, e.g. 5 to 8 wt.-%, of PVP, wherein said PVP consists of 3 to 8 wt.-%, e.g. 4 to 6 wt.-%, of a low molecular (<100 kDa) PVP component and 0 to 4 wt.-%, e.g. 1 to 3 wt.-%, of a high molecular (≥100 kDa) PVP component. In one embodiment, the total PVP contained in the spinning solution consists of from 22 to 34 weight-% and in particular from 25 to 30 weight-% of a high molecular weight (≥100 kDa) component and from 66 to 78 weight-%, in particular from 70 to 75 weight-% of a low molecular weight (<100 kDa) component. Examples for high and low molecular weight PVP are, for example, PVP K85/K90 and PVP K30, respectively.

In a particular embodiment, the polymer solution used in the process for preparing the membrane of the present invention further comprises 66-81 wt.-% of solvent and 0-10 wt.-%, e.g. 0-5 wt.-% of suitable additives. Suitable additives are, for example, chosen form the group of water, glycerol and/or other alcohols. Water is especially preferred and is present in the spinning solution in an amount of from 0 to 8 wt.-%, preferably in an amount of from 2 to 6 wt.-%. In one embodiment, the solvent used in the process is chosen from the group consisting of N-methylpyrrolidone (NMP), N-ethylpyrrolidone, N-octylpyrrolidone, dimethylacetamide (DMAC), dimethylsulfoxide (DMSO), dimethylformamide (DMF), butyrolactone and mixtures of said solvents. NMP is especially preferred. The spinning solution should be homogenously degassed and filtered.

The center fluid or bore liquid which is used for preparing the membrane according to the invention comprises at least one of the above-mentioned solvents and a precipitation medium chosen from the group of water, glycerol and other alcohols.

In certain embodiments, the center fluid additionally comprises a further additive to modify the surface of the membrane in order to further increase the performance of the membrane. In one embodiment of the invention, the amount of the additive in the center fluid is from 0.02 to 2 wt.-%, for example from 0.05 to 0.5 wt.-%, or from 0.05 to 0.25 wt.-%, based on the total weight of the center fluid.

Examples of suitable additives include hyaluronic acid and zwitterionic polymers as well as copolymers of a vinyl polymerizable monomer having a zwitterion in the molecule and another vinyl polymerizable monomer. Examples of zwitterionic (co)polymers include phosphobetaines, sulfobetaines, and carboxybetaines.

Examples of suitable phosphobetaines include polymers comprising phosphoryl choline groups, for instance copolymers of 2-methacryloyloxyethylphosphorylcholine (MPC) and other vinyl polymerizable monomers, e.g. vinylpyridine, vinylpyrrolidone, styrene, or (meth)acrylate derivatives like butyl methacrylate, n-dodecyl methacrylate, n-octadecyl methacrylate, benzyl methacrylate, hydroxypropyl methacrylate, and (3-trimethoxysilyl)propyl methacrylate. One particular example is poly((2-methacryloyloxyethyl-2'-trimethylammoniumethyl phosphate, inner salt)-co-(hydroxypropyl methacrylate)-co-(3-trimethoxysilyl propyl methacrylate)), e.g. in a proportion of about 76/18/5. Another particular example is poly((2-(methacryloyloxyethyl)-2'-trimethylammoniumethyl)phosphate, inner salt)-co-(n-dodecylmethacrylate)-co-(3-(trimethoxysilyl)propylmethacrylate)-co-(hydroxypropylmethacrylate)), e.g. in a proportion of about 23/47/5/25. Other examples are polycondensation products of a diamine monomer comprising a phosphoryl choline group, and, optionally, other diamine monomers, with a dicarboxylic acid or its derivatives, for instance copolymers of 2-(3,5-diaminophenylcarbonyloxy)ethyl phosphoryl choline, 4,4'-diamino-3,3'-dimethyldiphenylmethane, and isophthaloyl chloride, as described in Polym. J., Vol. 39 (2007) 712-721, incorporated herein by reference.

Examples of suitable sulfobetaines include sulfobetaines prepared from one or more monomers selected from the group consisting of sulfobetaine acrylates, sulfobetaine acrylamides, sulfobetaine vinyl compounds, sulfobetaine epoxides, and mixtures thereof; copolymers of vinylpyrrolidone and methacrylamidopropyl dimethylammonio propyl sulfobetaine (SPP); copolymers of vinylpyrrolidone and a (meth)acryloyloxyalkyl dialkyl ammonio alkyl sulfonate; or sulfobetaines based on polyvinylpyridines or polyvinylpyrrolidone. One particular example is poly(3-((2-methacryloyloxyethyl)dimethylammonio)propyl-1-sulfonate-co-vinylpyrrolidone), a copolymer of vinylpyrrolidone and 3-((2-methacryloyloxyethyl)dimethylammonio)propyl-1-sulfonate, also known as SPE, which is commercially available from Raschig GmbH, 67061 Ludwigshafen, Germany, under the trade name Ralu®Mer SPE. Another particular example is a copolymer of vinylpyrrolidone and 3-((2-acryloyloxyethyl)dimethylammonio)propyl-1-sulfonate, also known as SPDA, which is commercially available from Raschig GmbH, under the trade name Ralu®Mer SPDA. Another particular example is a polyvinylpyridine comprising pyridine-N-propylsulfonate and pyridine-N-oxide moieties.

Suitable carboxybetaines can be prepared from one or more monomers selected from the group consisting of carboxybetaine acrylates, carboxybetaine acrylamides, carboxybetaine vinyl compounds, carboxybetaine epoxides, and mixtures thereof. Other suitable polycarboxybetaine compounds are the products of the reaction of a poly(vinylpyrrolidone-covinylimidazole) with a vinylcarboxylic acid or a derivative thereof, for instance acrylic acid and its esters, methacrylic acid and its esters, crotonic acid and its esters, angelic acid and its esters, etc. Another example is the product of the reaction of a poly(vinylpyrrolidone-co-vinylimidazole) with a halocarboxylic acid or a derivative thereof. One particular example is the product of the reaction of a poly(vinylpyrrolidone-co-vinylimidazole) with acrylic acid, the poly(vinylpyrrolidone-co-vinylimidazole) being a copolymer of 50 mol-% vinylpyrrolidone and 50 mol-% vinylimidazole. Such a copolymer is commercially available from BASF SE under the trade name Luvitec® VPI 55, e.g. Luvitec® VPI 55 K72W or Luvitec® VPI 55 K18P.

The center fluid generally comprises 40-100 wt.-% precipitation medium and 0-60 wt.-% of solvent. In one embodiment the center fluid comprises 44-69 wt.-% precipitation medium and 29-54 wt.-% of solvent. In a particular embodiment, the center fluid comprises 49-61 wt.-% of water and 37-49 wt.-% of NMP. In another embodiment, the center fluid comprises 53-56 wt.-% of water and 44-47 wt.-% of NMP. The center fluid should also be degassed and filtered.

The viscosity of the polymer solution, measured according to DIN EN ISO 1628-1 at 22° C., usually is in the range of from 3,000 to 15,000 mPa·s, e.g., from 4,000 to 8,000 mPa·s, or even 4,900 to 5,900 mPa·s.

In one embodiment of the process for preparing the membrane of the present invention, the temperature of the spinneret is 50-70° C., e.g., 55-61° C., the temperature of the spinning shaft is 25-65° C., in particular 50-60° C. The distance between the opening of the nozzle and the precipitation bath is from 30 to 110 cm, in particular 45 to 55 cm. The precipitation bath has a temperature of 10-80° C., e.g. 20-40° C. In one embodiment, the spinning velocity is in the range of 15-100 m/min, in particular 25-45 m/min.

The polymer solution coming out through the outer slit opening of the spinning die is, on the outside of the precipitating fiber, exposed to a humid steam/air mixture comprising a solvent in a content of between 0 and 10 wt.-%, related to the water content.

The temperature of the humid steam/air mixture is at least 15° C., preferably at least 30° C., and at most 75° C., but is preferably not higher than 62° C. Further, the relative humidity in the humid steam/air mixture is between 60 and 100%.

In another embodiment of the process, the humid steam/air mixture comprises a solvent in an amount of between 0 and 5 wt.-%, related to the water content. Preferably, the humid steam/air mixture comprises a solvent in an amount of between 0 and 3 wt.-%, related to the water content. The effect of the solvent in the temperature-controlled steam atmosphere is to control the speed of precipitation of the fibers. If less solvent is employed, the outer surface will obtain a more dense surface, and if more solvent is used, the outer surface will have a more open structure. By controlling the amount of solvent within the temperature-controlled steam atmosphere surrounding the precipitating membrane, the amount and size of the pores on the outer surface of the membrane can be modified and controlled.

In one embodiment of the invention, the precipitation bath comprises from 85 to 100 wt-% of water and from 0 to 15 wt.-% of solvent, e.g. NMP. In another embodiment, the precipitation bath comprises from 90 to 100 wt.-% water and from 0 to 10 wt.-% NMP.

The membrane will then be washed to remove waste components and simultaneously or subsequently treated with a salt solution. In one embodiment, the membrane is first washed in at least one water bath and then treated in a further bath containing the salt solution. In a particular embodiment of a continuous process for producing the membrane of the invention, the membrane is first guided through five water baths and then through a sixth bath containing a salt solution.

In one embodiment of the invention, the concentration of the salt in the aqueous salt solution is in the range of from 0.5 to 12 wt.-%, e.g. 0.5 to 5 wt.-%. In a particular embodiment, an isotonic salt solution is used.

The salt in the aqueous salt solution preferably is a salt which is physiologically tolerable. In one embodiment of the invention, the salt is an alkali or alkaline earth salt, e.g. a lithium, sodium, potassium, magnesium, or calcium salt. In another embodiment, the salt is a zinc or iron salt. Examples of suitable anions are halide, e.g. fluoride, chloride or bromide, carbonate, sulfate, phosphate. In one embodiment, the salt is magnesium chloride. In another embodiment, the salt is sodium sulfate. In still another embodiment, the salt is sodium chloride. In a particular embodiment, isotonic saline solution is used.

The membrane is then dried at temperatures of 150-280° C., preferably 180-260° C. Such drying will provide for an adequate evaporation of water and a defined shrinkage of pores. The membrane can be dried discontinuously or continuously, the latter also being called "online-drying". In the online-drying process, the membrane is continuously fed to a dryer. The drying can be effected by any method known in the art. For instance, the membrane can be dried in a convection oven or by a stream of hot air, e.g. from a nozzle, by contact with a hot surface, or by irradiation, e.g. with infra-red or micro-wave radiation.

The final treatment consists of rinsing the membrane in water at a temperature of 50-95° C., preferably 80-90° C. and subsequent drying at temperatures of 30-65° C., preferably 55-65° C. As an alternative, the membrane can be dried after preparation of a membrane bundle.

In one embodiment, the membrane is steam-sterilized at temperatures above 121° C. for at least 21 minutes.

In one embodiment, the hollow fiber membrane of the invention has an inner diameter of from 180 to 250 µm, e.g. 186 to 194 µm. The wall thickness of the hollow fiber usually is in the range of from 10 to 50 µm, e.g. 34 to 36 µm.

Another aspect of the invention is a diffusion and/or filtration device comprising the membrane of the invention. Examples of such devices are dialyzers, hemofilters, and ultrafilters. Such devices generally consist of a casing comprising a tubular section with end caps capping the mouths of the tubular section. A bundle of hollow fiber membranes is usually arranged in the casing in a way that a seal is provided between the first flow space formed by the fiber cavities and a second flow space surrounding the membranes on the outside. Examples of such devices are disclosed in EP 0 844 015 A2, EP 0 305 687 A1, and WO 01/60477 A2, all incorporated herein by reference.

Another aspect of the invention is the use of the membrane of the invention in hemodialysis, hemodiafiltration or hemofiltration of blood. The membrane of the invention can be used for these purposes instead of conventional membranes, but in a similar manner. The person skilled in the art will easily derive the necessary modus operandi.

Another aspect of the invention is the use of the membrane of the invention in bioprocessing, plasma fractionation and the preparation of protein solutions. The membrane of the invention can be used for these purposes instead of membranes conventionally used for these purposes. The person skilled in the art will easily derive a suitable modus operandi for the intended application.

It will be understood that the features mentioned above and those described hereinafter can be used not only in the combination specified but also in other combinations or on their own, without departing from the scope of the present invention.

The present invention will now be described in more detail in the examples below. The examples are not intended to limit the scope of the present invention, but are merely an illustration of particular embodiments of the invention.

Analytical Methods
i) Membrane Bundle Preparation
[A] Preparation of Hand Bundles:

The preparation of the membrane bundle after the spinning process is necessary to prepare the fiber bundle for the following performance tests. The first process step is to cut the fiber bundles to a defined length of 23 cm. The next process step consists of melting the ends of the fibers. An optical control ensures that all fibers are well melted. Then, the ends of the fiber bundle are transferred into a potting cap. The potting cap is fixed mechanically and a potting tube is put over the potting caps. Then the fibers are potted with polyurethane. After the polyurethane has hardened, the potted membrane bundle is cut to a defined length and stored dry before it is used for the different performance tests.

[B] Preparation of Mini-Modules:

Mini-modules [=fiber bundles in a housing] are prepared in a similar manner. The mini-modules ensure protection of the fibers and are used for steam-sterilization with residual water on the fiber. The manufacturing of the mini-modules differs in the following points:

The number of fibers required is calculated for an effective surface A of 360 cm² according to equation (1)

$$A = \pi \times d_i \times l \times n \; [\text{cm}^2] \tag{1}$$

with
$d_i$=inner diameter of fiber [cm]
n=amount of fibers
l=effective fiber length [cm]

The fiber bundle is cut to a defined length of 20 cm

The fiber bundle is transferred into the housing before the melting process

The mini-module is put into a vacuum drying oven over night before the potting process

[C] Preparation of Filters:

The filter (=dialyzer) comprises about 8,000 to 10,000 fibers with an effective surface area of 1.4 m². A filter is characterized by a cylindrical housing with two connectors for the dialyzing fluid and caps applied on both ends, each with one centered blood connector. The manufacturing process (after winding) can be divided into the following main steps:

the cut bundles (length approx. 30 cm) are transferred into the housing with a special bundle claw;

both ends of the bundles are closed by a closing process the fibers are potted into the housing with polyurethane (PUR);

the ends are cut to open the fibers;

the caps are welded to the blood connectors using ultrasonic welding;

final treatment comprises: rinsing, integrity testing, final drying the filters are packed in sterile bags and steam sterilized.

Ii) Hydraulic Permeability (Lp) of Hand Bundles and Mini-Modules

The hydraulic permeability of a membrane bundle is determined by pressing a defined volume of water under pressure through the membrane bundle, which has been sealed on one side, and measuring the required time. The hydraulic permeability can be calculated from the determined time, the effective membrane surface area, the applied pressure and the volume of water pressed through the membrane. From the number of fibers, the fiber length as well as the inner diameter of the fiber, the effective membrane surface area is calculated. The membrane bundle has to be wetted thirty minutes before the Lp-test is performed. For this purpose, the membrane bundle is put in a box containing 500 ml of ultrapure water. After 30 minutes, the membrane bundle is transferred into the testing system. The testing system consists of a water bath that is maintained at 37° C. and a device where the membrane bundle can be mounted. The filling height of the water bath has to ensure that the membrane bundle is located underneath the water surface in the designated device. To avoid that a leakage of the membrane leads to a wrong test result, an integrity test of the membrane bundle and the test system has to be carried out in advance. The integrity test is performed by pressing air through the membrane bundle that is closed on one side of the bundle. Air bubbles indicate a leakage of the membrane bundle or the test device. It has to be checked if the leakage is due to an incorrect mounting of the membrane bundle in the test device or if a real membrane leakage is present. The membrane bundle has to be discarded if a leakage of the membrane is detected. The pressure applied in the integrity test has to be at least the same value as the pressure applied during the determination of the hydraulic permeability in order to ensure that no leakage can occur during the measurement of the hydraulic permeability because the pressure applied is too high.

iii) Hydraulic Permeability (Lp) Of Filters

The hydraulic permeability of a filter is determined by flowing a defined volume of water through the membrane and measuring the trans-membrane pressure. Before starting the measurement, the filter has to be totally filled (inside the membrane and the compartment between the housing and the membranes) with the testing fluid. Air is removed by gentle tapping. The testing fluid, a solution of sodium chloride in pure water having a concentration of 0.9 wt.-%, is heated to 38° C. and then pumped through the blood inlet of the filter, while the blood exit connector and the inlet of the dialyzed connection are closed. The measurement takes 5 minutes and average values for the pressures are calculated. The calculation of the hydraulic permeability is performed as described in ii).

iv) Diffusion Experiments on Hand Bundles

Diffusion experiments with isotonic chloride solution (0.9 wt.-%), vitamin B12 diluted in dialysis fluid (100 mg/l) and albumin in PBS buffer (100 mg/l) are carried out to determine the diffusion properties of a membrane. A hand bundle is put in a measuring cell. The measuring cell allows passing the particular solution at the inside of the hollow fiber. Additionally, the measuring cell is filled completely with water and a high cross-flow of distilled water is set to carry away the particular ions that pass the membrane cross-section from the inside of the hollow fiber to the outside. By adjusting the pressure ratios correctly, a zero filtration is aimed for, so that only the diffusion properties of the membrane are determined (by achieving the maximum concentration gradient of the particular ion between the inside of the hollow fiber and the surrounding of the hollow fiber) and not a combination of diffusive and convective properties. A sample from the pool is taken at the beginning and a sample of the retentate is taken after 10 and 20 minutes. The chloride samples are then titrated with silver nitrate solution to determine the chloride concentration. The vitamin B12 samples are analyzed photometrically and the albumin samples are analyzed using an Autoanalyzer (Mira Plus, ABX Diagnostics, Cobas, Roche). From the concentrations determined, the effective membrane surface area A and the flow conditions, the permeability P, of chloride, vitamin B12, or albumin, respectively, can be calculated according to the following equation (2):

$$P_x [10^{-4} \text{ cm/s}] = [Q_B/60/A] * \ln [(c_A - c_D)/c_R] * 10^4 \quad (2)$$

with
P=diffusive permeability [cm/s]
c=concentration [mmol]
A=effective membrane surface [cm²]
indices:
x=substance (here: chloride, vitamin B12 or albumin, respectively)
A=starting concentration (feed)
D=dialysate
R=retentate
$Q_B$=blood flow [ml/min]

v) Selectivity/Sieving Coefficient (SC) for Proteins of Hand Bundles, Mini-Modules and Filters The selectivity of a membrane is determined by sieving coefficient measurements. For this purpose, the medium in which the protein (here myoglobin from horse heart, MW=17.5 kDa; ovalbumin, MW=44 kDa; and albumin, MW=66 kDa) is dissolved is of crucial importance. The media used in this testing procedure is PBS buffer with a pH of 7.2. In general, the sieving coefficient of the particular molecule is obtained as follows: The particular protein solution is maintained at a temperature of 37° C.±1° C. and pumped under defined conditions (blood flow ($Q_B$), TMP and filtration rate (UF)) through the testing device (hand bundles, mini-modules or filters). Then, the concentration of the protein in the feed (in), in the retentate (r) and in the filtrate (f) is determined and the sieving coefficient (SC) can then be calculated according to the following equation (3):

$$SC[\%] = 2 * c(f) / [c(\text{in}) + c(r)] * 100\% \quad (3)$$

If the concentration of the protein in the filtrate is zero, a sieving coefficient of 0% is obtained. If the concentration of the protein in the filtrate equals the concentration of the protein in the feed and the retentate, a sieving coefficient of 100% is obtained.

[A] Sieving Coefficient in Aqueous Solution on Hand Bundles and Mini-Modules

The Sieving Coefficient experiments in aqueous solution of myoglobin, ovalbumin and albumin are performed using two different experimental set-ups with separate solutions. First, the sieving coefficient of either myoglobin or ovalbumin is determined. Then the sieving coefficient of albumin is determined.

The concentration of myoglobin or ovalbumin, respectively, in the PBS buffer is 100 mg/l. The expiry date of the aqueous solution is between 4 and 8 weeks. The solution has to be stored in the refrigerator. Prior to the Sieving Coefficient experiment, an Lp-test is performed as described above. The sieving coefficient experiment for myoglobin or ovalbumin, respectively, is run in single pass with testing conditions defined as follows:

The intrinsic flow rate ($J_v$ in cm/s) and wall shear rate ($\gamma$ in s$^{-1}$) are fixed whereas the blood flow ($Q_B$) and filtration rate (UF) is calculated using equations (4) and (5), respectively:

$$Q_B \text{ [ml/min]} = \gamma * n * \pi * d_i^3 * 60/32 \quad (4)$$

$$UF \text{ [ml/min]} = J_V * A * 60 \quad (5)$$

with
n=amount of fibers
$d_i$=inner diameter of fiber [cm]
$\gamma$=shear rate [s$^{-1}$]
A=effective membrane surface [cm²]
wherein A is calculated according to equation (1).

When testing a hand bundle or a mini-module, the shear rate is set to 500 s$^{-1}$ and the intrinsic flow rate is defined to be 0.38*10$^{-04}$ cm/s.

The first samples are taken after 15 minutes (pool, retentate, and filtrate) and a second time after 60 min. At the end, the test-bundle is rinsed for some minutes with PBS-buffer, then the test is stopped.

Subsequently, the SC-test of albumin is performed. 60 g of albumin are dissolved in PBS-buffer and the experiment is run re-circulating, the albumin solution being slowly stirred by a magnetic bar stirrer. In the test set-up, the $Q_B$ is calculated according to equation (4), a fixed TMP of 400 mmHg is set and the UF as well as the retentate flow is a result of the test conditions and the membrane permeability properties. After 15 minutes, the flow is switched to single-pass and samples (pool, retentate, filtrate) are taken. After the SC-test the test-bundle can be rinsed once more with PBS-buffer and used to perform a second Lp-test in order to get an indication of the adsorption capacity of the membrane for the protein.

[B] Sieving Coefficient in Aqueous Solution on Filters

In contrast to [A], the measurement of the sieving coefficient of myoglobin, ovalbumin and albumin on filters is performed with the same test set-up but with separate solutions. The solution is re-circulated. The concentration of myoglobin and ovalbumin, respectively, is 125 mg/l and the concentration of albumin is 250 mg/l. The intrinsic flow rate ($J_v$ in cm/s) and wall shear rate ($\gamma$ in s$^{-1}$) are fixed whereas the blood flow ($Q_B$) and the filtration rate (UF) are calculated using equations (6) and (5), respectively:

$$Q_B \text{ [ml/min]} = \gamma * n * \pi * di^3 * 60/32 + J_v * A * 30 \quad (6)$$

with $$\gamma = 461 \text{ s}^{-1} \text{ and } J_v = 0.704 * 10^{-04} \text{ cm/s}.$$

Sample taking for both substances is the same as in [A] with the difference that the second sample is taken after 30 minutes (not after 60 minutes).

vi) Clearance of Urea/Vitamin B12 on Filters

Clearance of urea (MW=60 Da) and vitamin B12 (MW=1, 355 Da), respectively, on filters is measured on a dialysis machine using dialysis solution (dialysis concentrate diluted in degassed water) heated to 37° C.±1° C. The dialysis solution comprising the particular substances is pumped through the blood side, pure dialysis fluid flows in the dialysate compartment, and the mass transfer from blood to dialysate side is determined. Both flows are operated in single pass. The starting concentration of urea is set to 1 g/l and the concentration of vitamin B12 is set to 50 mg/l, diluted in the same dialysis fluid. The following parameters are set:

$Q_B$=400 ml/min
$Q_D$=500 ml/min
UF=0 ml/min

The first samples are taken after 10 minutes and samples from $Q_{B, in}$, $Q_{B, out}$ as well as $Q_{D, out}$ (for proofing the mass balance) are taken.

The Clearance Cl can be calculated according to equation (7):

$$Cl = (Q_{B,in} * c_{B,in} - Q_{B,out} * c_{B,out})/c_{B,in} \quad (7)$$

vii) UF Plasma/Protein Loss on Filters

This performance test determines the protein loss as well as the filtration rate for a fixed blood flow of plasma on filters. The protein concentration of the plasma is set to 60 g/l±2 g/l. The plasma has to have a viscosity of 1.59±0.05 mm²/s as determined by a capillary, as well as a hematocrit of 30±1%, and is heated to 37° C.±1° C. Before starting the test, the filter is rinsed with isotonic saline. Then, the plasma is re-circulated through the blood side and the measurement begins. Within 10 minutes, $Q_B$=300 ml/min and TMP=300 mmHg are set. Samples of the filtrate are taken after 25 minutes and UF is determined volumetrically. The protein concentration of the filtrate Pct is then analyzed which relates to protein loss.

EXAMPLES

The dynamic viscosity η of the polymer solutions was determined according to DIN ISO 1628-1 at a temperature of 22° C. using a capillary viscometer (ViscoSystem® AVS 370, Schott-Gerate GmbH, Mainz, Germany).

Example 1

A polymer solution was prepared by dissolving polyethersulfone (Ultrason® 6020, BASF Aktiengesellschaft) and polyvinylpyrrolidone (K30 and K85, BASF Aktiengesellschaft) and distilled water in N-methylpyrrolidone (NMP). The weight fraction of the different components in the polymer spinning solution was: PES-PVP K85-PVP K30-H$_2$O-NMP=14-2-5-3-76. The viscosity of the polymer solution was 4,967 mPaxs.

The sequence of adding the polymer material to the solvent, the temperature and the stirring time are important. A clear solution without any turbidity and bubbles is subsequently needed for a uniform morphology and performance of the membrane. Particles or bubbles in the polymer solution disturb the coagulation process and can lead to defects in membrane structure.

To prepare the solution, NMP and water were first filled into a three neck-flask with finger-paddle agitator in the center neck. The PVP was added to the NMP and stirred at 50° C. until a homogeneous clear solution was obtained. Finally, the polyethersulfone was added. The mixture was stirred at 50° C. until a clear highly viscous solution was obtained. The warm solution was cooled to 20° C. and degassed. To fully degas the solution, the highly viscous polymer solution was transferred to a stainless steel container. After transferring the solution to the container, the container was closed tightly and vacuum was applied to the container. The solution was degassed at 50 mmHg for 6 hours. During this degassing procedure the container was agitated to create a larger surface and thinner film thickness of the polymer solution in the container in order to improve the degassing.

A bore liquid was prepared by mixing distilled water and N-Methylpyrrolidone (NMP). The weight fraction of the two components in the center fluid was: H$_2$O-NMP=55%-45%.

The preparation of the bore liquid was carried out as follows:

Distilled water was filled into a glass flask and heated to 50° C.;
NMP was added and stirred for approximately 1 hour;
The clear mixture was transferred to a stainless steel container;
The mixture was filtered and degassed at 50 mmHg A membrane was formed by heating the polymer solution to 50° C. and passing the solution as well as the bore liquid through a spinning die. The temperature of the die was 55° C. and of the spinning shaft was 53° C. The hollow fiber membrane was formed at a spinning speed of 25 m/min. The liquid capillary leaving the die was passed into a water bath (ambient temperature). The distance between the die and the precipitation bath was 50 cm. The hollow fiber membrane formed was guided through 5 different water baths and an additional sixth bath with 0.9 wt.-% NaCl solution and then fed to an online dryer.

The dry hollow fiber membrane had an inner diameter of 192 μm and an outer diameter of 262 μm and a fully asymmetric membrane structure. The active separation layer of the membrane was at the inner side. The active separation layer is defined as the layer with the smallest pores. The membranes were wound on a winding wheel and mini-modules with 356 fibers were prepared according to the method described above.

Unsterile Membranes (Hand Bundles):

The diffusive permeabilities of chloride, vitamin B12 and albumin were measured in aqueous solution on unsterile hand bundles (n=200) as described above. The results are given in Table 13.

Steam Sterilized Membranes (Mini-Modules):

The performance of the membrane was measured on steam-sterilized mini-modules (methods described above). Hydraulic permeability as well as sieving coefficient of myoglobin, ovalbumin and albumin in aqueous solution was tested. The results as well as the comparison data of Comparative example 1 are shown in Table 1.

TABLE 1

Lp value, SC of myoglobin, ovalbumin and albumin measured in aqueous solution.

| Membrane | Lp [$10^{-04}$*cm/ bar*s] | Sieving coefficient in aqueous solution [%] | | | | |
| --- | --- | --- | --- | --- | --- | --- |
| | | Myoglobin, 17 kD | | Ovalbumin, 44 kD | | Albumin, 66 kD |
| | | 15' | 60' | 15' | 60' | 15' |
| Comparative Example 1 | 85.7 | 94.1 | 93.0 | 49.1 | 31.9 | 3.4 |
| Example 1 | 138.3 | 92.6 | 93.0 | 66.1 | 58.4 | 6.4 |

Figure 2:
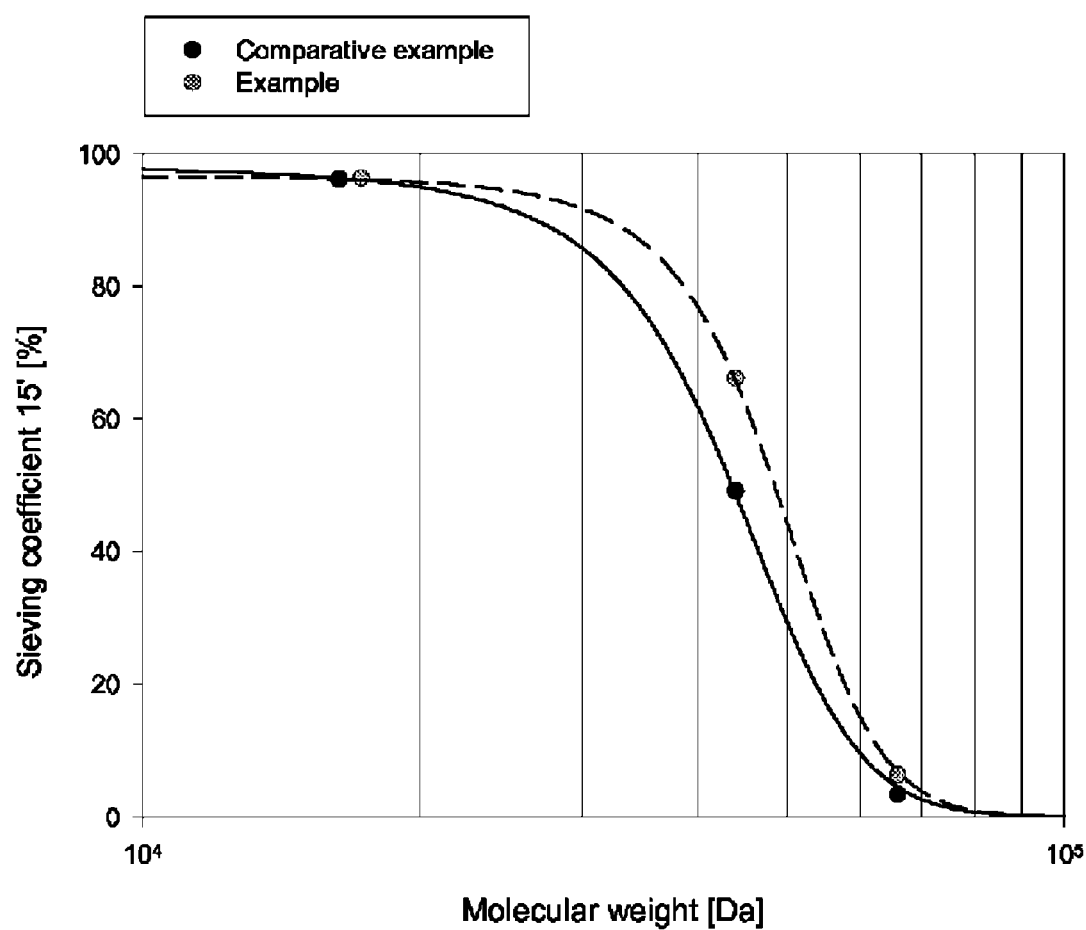
FIG. 2 shows the sieving profiles of the membrane of Example 1 and Comparative example 1.

FIG. 2 shows the sieving profiles of the membrane of Example 1 and Comparative example 1, created by the measured sieving coefficients after 15' in aqueous solution of myoglobin, ovalbumin and albumin, assuming that the sieving coefficient for a molecule of MW 100 Da is 100% and the sieving coefficient of a molecule of MW 1,000 kDa is 0%.

Example 2

A membrane was produced using a polymer solution having the same composition as in Example 1 and a viscosity of 5,371 mPa×s. The preparation of the polymer solution was conducted as described in Example 1. The membrane formation procedure was changed in the following points:

Composition of bore liquid: $H_2O$-NMP: 56%-44%;

Temperature of the die/spinning shaft: 57/55° C.

The dry hollow fiber membrane had an inner diameter of 192 μm and an outer diameter of 262 μm and a fully asymmetric membrane structure. The active separation layer of the membrane was at the inner side.

Unsterile Membranes (Hand Bundles):

The diffusive permeabilities of chloride, vitamin B12 and albumin were measured in aqueous solution on unsterile hand bundles (n=200) as described above. The results are given in Table 13.

Steam Sterilized Membranes (Mini-Modules):

The performance of the membrane was measured on steam-sterilized mini-modules (methods described above). Hydraulic permeability as well as sieving coefficient of myoglobin, ovalbumin and albumin in aqueous solution was tested. The results as well as the comparison data of Comparative example 1 are shown in Table 2.

TABLE 2

Lp value, SC myoglobin, ovalbumin and albumin values measured in aqueous solution.

| Membrane | Lp [$10^{-04}$*cm/ bar*s] | Sieving coefficient in aqueous solution [%] | | | | |
| --- | --- | --- | --- | --- | --- | --- |
| | | Myoglobin, 17 kD | | Ovalbumin, 44 kD | | Albumin, 66 kD |
| | | 15' | 60' | 15' | 60' | 15' |
| Comparative Example 1 | 85.7 | 94.1 | 93.0 | 49.1 | 31.9 | 3.4 |
| Example 2 | 129.5 | 95.5 | 94.9 | 62.0 | 43.5 | 5.3 |

Figure 3:
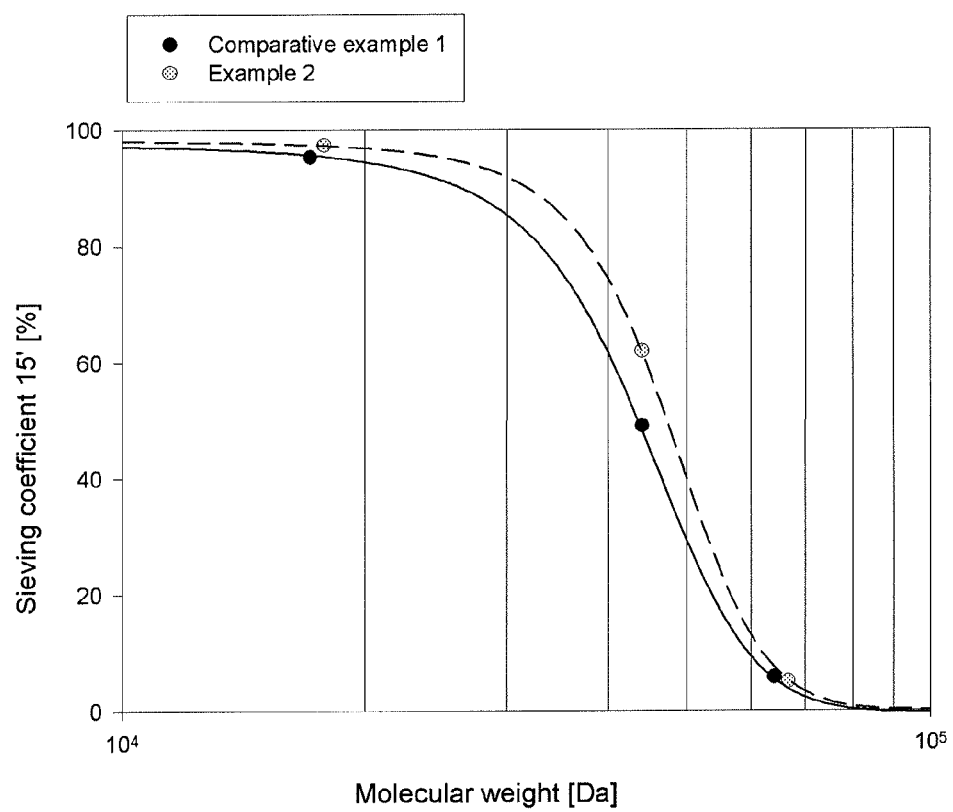
FIG. 3 shows the sieving profiles of the membrane of Example 2 and Comparative example 1.

FIG. 3 shows the sieving profiles of the membrane of Example 2 and Comparative example 1, created by the measured sieving coefficients after 15' in aqueous solution of myoglobin, ovalbumin and albumin, assuming that the sieving coefficient for a molecule of MW 100 Da is 100% and the sieving coefficient of a molecule of MW 1,000 kDa is 0%.

Example 3

A membrane was produced using a polymer solution having the same composition as in Example 1 and a viscosity of 5,371 mPa×s. The preparation of the polymer solution was conducted as described in Example 1. The membrane formation procedure was changed in the following points:

Composition of bore liquid: $H_2O$-NMP: 56%-44%

Temperature of the die/spinning shaft: 59/57° C.

The dry hollow fiber membrane had an inner diameter of 192 μm and an outer diameter of 262 μm and a fully asymmetric membrane structure. The active separation layer of the membrane was at the inner side.

Unsterile Membranes (Hand Bundles):

The diffusive permeabilities of chloride, vitamin B12 and albumin were measured in aqueous solution on unsterile hand bundles (n=200) as described above. The results are given in Table 13.

Steam Sterilized Membranes (Mini-Modules):

The performance of the membrane was measured on steam-sterilized mini-modules (methods described above). Hydraulic permeability as well as sieving coefficient of myoglobin, ovalbumin and albumin in aqueous solution was tested. The results as well as the comparison data of Comparative example 1 are shown in Table 3.

TABLE 3

Lp value, SC myoglobin, ovalbumin and albumin values measured in aqueous solution.

| Membrane | Lp [$10^{-04}$*cm/ bar*s] | Sieving coefficient in aqueous solution [%] | | | | |
| --- | --- | --- | --- | --- | --- | --- |
| | | Myoglobin, 17 kD | | Ovalbumin, 44 kD | | Albumin, 66 kD |
| | | 15' | 60' | 15' | 60' | 15' |
| Comparative Example 1 | 85.7 | 94.1 | 93.0 | 49.1 | 31.9 | 3.4 |
| Example 3 | 138.2 | 95.2 | 96.3 | 58.8 | 49.2 | 5.7 |

Figure 4:
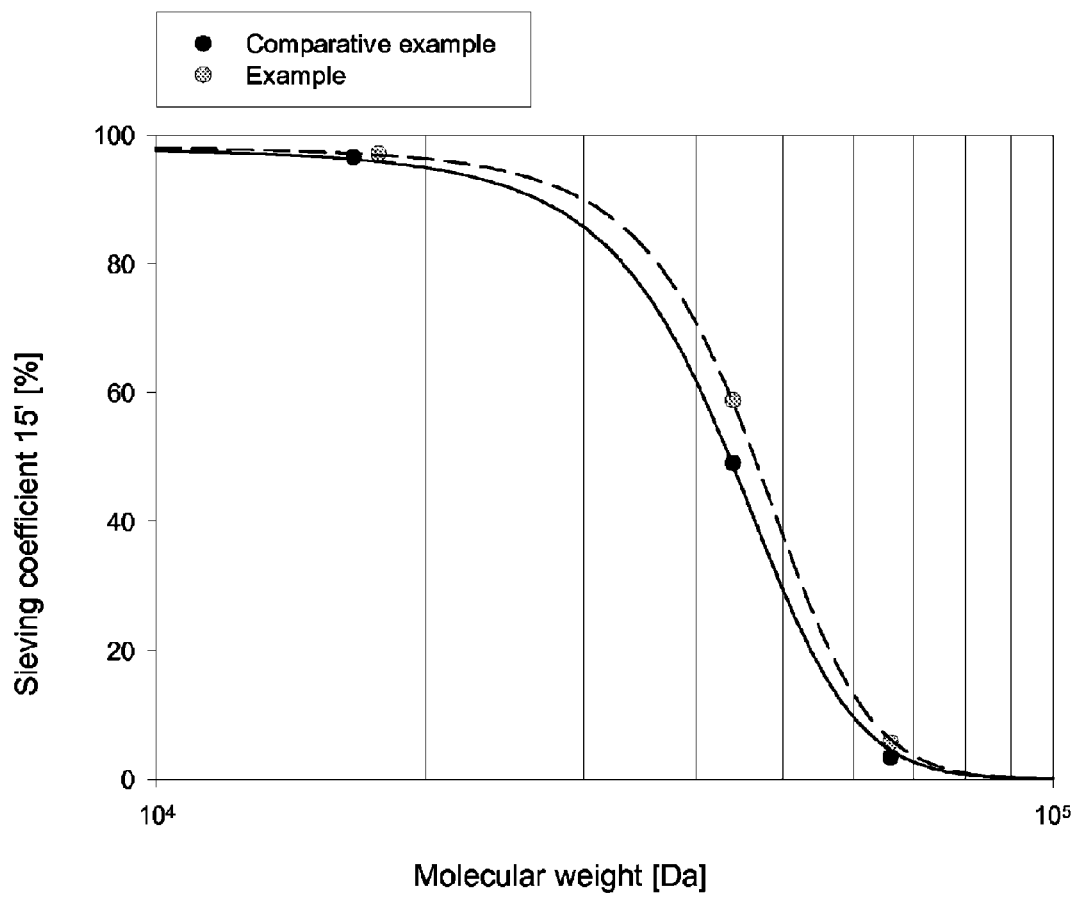
FIG. 4 shows the sieving profiles of the membrane of Example 3 and Comparative example 1.

FIG. 4 shows the sieving profiles of the membrane of Example 3 and Comparative example 1, created by the measured sieving coefficients after 15' in aqueous solution of myoglobin, ovalbumin and albumin, assuming that the sieving coefficient for a molecule of MW 100 Da is 100% and the sieving coefficient of a molecule of MW 1,000 kDa is 0%.

Example 4

A membrane was produced using a polymer solution having the same composition as in Example 1 and a viscosity of 5,822 mPa×s. The preparation of the polymer solution was conducted as described in Example 1. The membrane formation procedure was changed in the following points:

Composition of bore liquid: $H_2O$-NMP: 56%-44%;
Spinning speed: 45 m/min;
Temperature of the die/spinning shaft: 59/57° C.;

The dry hollow fiber membrane had an inner diameter of 191 μm and an outer diameter of 261 μm and a fully asymmetric membrane structure. The active separation layer of the membrane was at the inner side.

Unsterile Membranes (Hand Bundles):

The diffusive permeabilities of chloride, vitamin B12 and albumin were measured in aqueous solution on unsterile hand bundles (n=200) as described above. The results are given in Table 13.

Steam Sterilized Membranes (Mini-Modules):

The performance of the membrane was measured on steams-terilized mini-modules (methods described above). Hydraulic permeability as well as sieving coefficient of myoglobin, ovalbumin and albumin in aqueous solution was tested. The results as well as the comparison data of Comparative example 1 are shown in Table 4.

TABLE 4

Lp value, SC myoglobin, ovalbumin and albumin values measured in aqueous solution.

|  | Lp $[10^{-04}*$cm/ bar*s] | Sieving coefficient in aqueous solution [%] | | | | |
| --- | --- | --- | --- | --- | --- | --- |
|  |  | Myoglobin, 17 kD | | Ovalbumin, 44 kD | | Albumin, 66 kD |
| Membrane |  | 15' | 60' | 15' | 60' | 15' |
| Comparative Example 1 | 85.7 | 94.1 | 93.0 | 49.1 | 31.9 | 3.4 |
| Example 4 | 177.0 | 98.1 | 98.0 | 61.3 | 51.5 | 5.6 |

Figure 5:
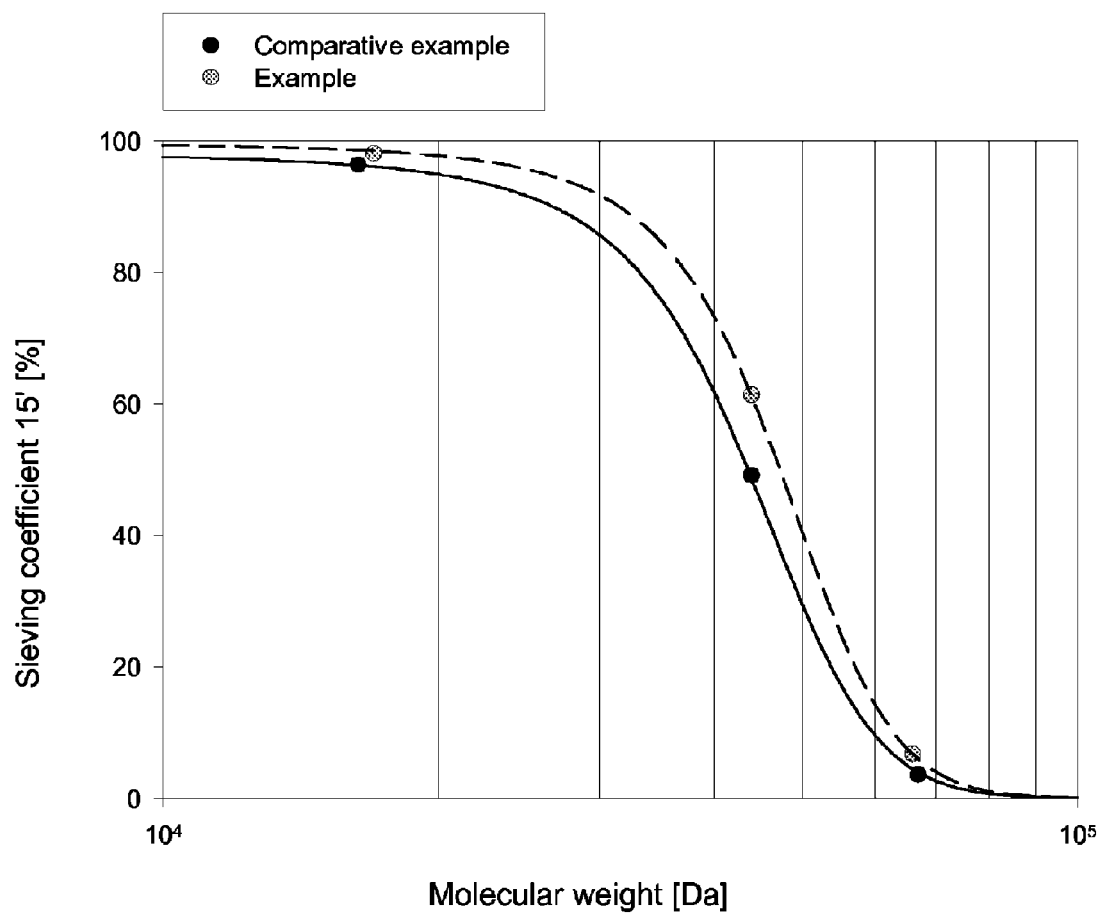
FIG. 5 shows the sieving profiles of the membrane of Example 4 and Comparative example 1.

FIG. 5 shows the sieving profiles of the membrane of Example 4 and Comparative example 1, created by the measured sieving coefficients after 15' in aqueous solution of myoglobin, ovalbumin and albumin, assuming that the sieving coefficient for a molecule of MW 100 Da is 100% and the sieving coefficient of a molecule of MW 1,000 kDa is 0%.

COMPARATIVE EXAMPLES

Comparative Example 1

A polymer solution was prepared by dissolving polyethersulfone (BASF Ultrason 6020), polyvinylpyrrolidone (BASF K30 and K85) and distilled water in N-Methylpyrrolidone (NMP). The weight fraction of the different components in the polymer spinning solution was: PES-PVP K85-PVP K30-$H_2O$-NMP: 14-2-5-3-76. The viscosity of the polymer solution was 5,010 mPa×s.

The remaining process steps were kept as in Example 1. The membrane formation procedure was changed in the following points:

Composition of bore liquid: $H_2O$-NMP 54.5%-45.5%;
Spinning speed: 50 m/min;
Temperature of the die: 55/53° C.;
The membrane was dried in an online-dryer.

The dried hollow fibre membrane had an inner diameter of 190 μm and an outer diameter of 260 μm and a fully asymmetric membrane structure. The active separation layer of the membrane was at the inner side.

Unsterile Membranes (Hand Bundles):

The diffusive permeabilities of chloride, vitamin B12 and albumin were measured in aqueous solution on unsterile hand bundles (n=200) as described above. The results are given in Table 13.

Sterile Membranes (Mini-Modules):

The sieving coefficients of myoglobin, ovalbumin and albumin in aqueous solution were tested on steam-sterilized mini-modules (methods described above). The results are shown in Table 5.

TABLE 5

Lp value, SC of myoglobin, ovalbumin and albumin measured in aqueous solution.

|  | Lp $[10^{-04}*$cm/ bar*s] | Sieving coefficient in aqueous solution [%] | | | | |
| --- | --- | --- | --- | --- | --- | --- |
|  |  | Myoglobin, 17 kD | | Ovalbumin, 44 kD | | Albumin, 66 kD |
| Membrane |  | 15' | 60' | 15' | 60' | 15' |
| Comparative Example 1 | 85.7 | 94.1 | 93.0 | 49.1 | 31.9 | 3.4 |

Comparative Example 2

A polymer solution was prepared by dissolving polyethersulfone (BASF Ultrason 6020), polyvinylpyrrolidone (BASF K30 and K85) and distilled water in N-Methylpyrrolidone (NMP). The weight fraction of the different components in the polymer spinning solution was: PES-PVP K85-PVP K30-$H_2O$-NMP: 14-2-5-2-77. The viscosity of the polymer solution was 5,378 mPa×s.

The remaining process steps were kept as in Example 1. The membrane formation procedure was changed in the following points:

Composition of bore liquid: $H_2O$-NMP 53%-47%;
Spinning speed: 45 m/min;
Temperature of the die: 58/54° C.;
The membranes were dried in an online-dryer.

The dried hollow fibre membrane had an inner diameter of 215 μm and an outer diameter of 315 μm and a fully asymmetric membrane structure. The active separation layer of the membrane was at the inner side.

Unsterile Membranes (Hand Bundles):

The diffusive permeabilities of chloride, vitamin B12 and albumin were measured in aqueous solution on unsterile hand bundles (n=200) as described above. The results are given in Table 13.

Sterile Membranes (Mini-Modules):

The sieving coefficients of myoglobin, ovalbumin and albumin in aqueous solution were tested on steam-sterilized mini-modules (methods described above). The results are shown in Table 6.

TABLE 6

Lp value, SC of myoglobin, ovalbumin and albumin measured in aqueous solution.

| | | Sieving coefficient in aqueous solution [%] | | | | |
|---|---|---|---|---|---|---|
| | Lp [$10^{-04}$*cm/ | Myoglobin, 17 kD | | Ovalbumin, 44 kD | | Albumin, 66 kD |
| Membrane | bar*s] | 15' | 60' | 15' | 60' | 15' |
| Comparative Example 2 | 439.3 | 98.7 | 98.3 | 84.9 | 88.1 | 37.4 |

Comparative Example 3

Membranes were cut out of a commercially available Nipro PES-15Sα (Nipro Corp., 3-9-3 Honjo-Kishi, Kita-ku, Osaka 531-8510, Japan) filter and mini-modules comprising 337 fibres were prepared ($A_{eff}$=360 cm$^2$). The membranes had an inner diameter of 200 μm and a width of 40 μm. The membranes are gamma-sterilized.

Sterile Membranes (Mini-Modules):

The sieving coefficients of myoglobin, ovalbumin and albumin in aqueous solution were tested using mini-modules comprising membranes taken out of a sterile filter (methods described above). The results are shown in Table 7.

TABLE 7

Lp value, SC of myoglobin, ovalbumin and albumin measured in aqueous solution.

| | | Sieving coefficient in aqueous solution [%] | | | | |
|---|---|---|---|---|---|---|
| | Lp [$10^{-04}$*cm/ | Myoglobin, 17 kD | | Ovalbumin, 44 kD | | Albumin, 66 kD |
| Membrane | bar*s] | 15' | 60' | 15' | 60' | 15' |
| Comparative Example 3 | 111.2 | 94.4 | 95.5 | 67.4 | 56.8 | 19.4 |

Comparative Example 4

Membranes were cut out of a commercially available FX 100 filter (Fresenius Medical Care AG, 61346 Bad Homburg, Germany) and mini-modules comprising 381 fibres were prepared ($A_{eff}$=360 cm$^2$). The membranes had an inner diameter of 177 μm and a width of 37 μm.

Sterile Membranes (Mini-Modules):

The sieving coefficients of myoglobin, ovalbumin and albumin in aqueous solution were tested using mini-modules comprising membranes taken out of a sterile filter (methods described above). The results are shown in Table 8.

TABLE 8

Lp value, SC of myoglobin, ovalbumin and albumin measured in aqueous solution.

| | | Sieving coefficient in aqueous solution [%] | | | | |
|---|---|---|---|---|---|---|
| | Lp [$10^{-04}$*cm/ | Myoglobin, 17 kD | | Ovalbumin, 44 kD | | Albumin, 66 kD |
| Membrane | bar*s] | 15' | 60' | 15' | 60' | 15' |
| Comparative Example 4 | 27.0 | 69.6 | 57.8 | 7.8 | 6.7 | 2.7 |

Comparative Example 5

Membranes were cut out of a commercially available Nipro Sureflux® 150 FH GA (Nipro Corp., 3-9-3 Honjo-Kishi, Kita-ku, Osaka 531-8510, Japan) filter and mini-modules comprising 368 fibres were prepared ($A_{eff}$=360 cm$^2$). The membranes had an inner diameter of 183 μm and a width of 17 μm. The membranes are gamma-sterilized.

Sterile Membranes (Mini-Modules):

The sieving coefficients of myoglobin, ovalbumin and albumin in aqueous solution were tested using mini-modules comprising membranes taken out of a sterile filter (methods described above). The results are shown in Table 9.

TABLE 9

Lp value, SC of myoglobin, ovalbumin and albumin measured in aqueous solution.

| | | Sieving coefficient in aqueous solution [%] | | | | |
|---|---|---|---|---|---|---|
| | Lp [$10^{-04}$*cm/ | Myoglobin, 17 kD | | Ovalbumin, 44 kD | | Albumin, 66 kD |
| Membrane | bar*s] | 15' | 60' | 15' | 60' | 15' |
| Comparative Example 5 | 77.9 | 93.1 | 98.1 | 54.6 | 51.8 | 19.6 |

Comparative Example 6

Membranes were cut out of a commercially available Baxter CA 150G (Baxter S. A., Renal Division, 78310 Maurepas, France) filter and mini-modules comprising 455 fibres were prepared ($A_{eff}$=360 cm$^2$). The membranes had an inner diameter of 148 μm and a width of 12 μm.

Sterile Membranes (Mini-Modules):

The sieving coefficients of myoglobin, ovalbumin and albumin in aqueous solution were tested using mini-modules comprising membranes taken out of a sterile filter (methods described above). The results are shown in Table 10.

TABLE 10

Lp value, SC of myoglobin, ovalbumin and albumin measured in aqueous solution.

| | | Sieving coefficient in aqueous solution [%] | | | | |
|---|---|---|---|---|---|---|
| | Lp [$10^{-04}$*cm/ | Myoglobin, 17 kD | | Ovalbumin, 44 kD | | Albumin, 66 kD |
| Membrane | bar*s] | 15' | 60' | 15' | 60' | 15' |
| Comparative Example 6 | 1.7 | 4.9 | 5.3 | <1.9* | <1.9* | <0.05* |

*below detection limit

Comparative Example 7

Membranes were cut out of a commercially available Baxter Xenium® 210 (Baxter S. A., Renal Division, 78310 Maurepas, France) filter and mini-modules comprising 351 fibres were prepared ($A_{eff}$=360 cm$^2$). The membranes had an inner diameter of 192 μm and a width of 34 μm.

Sterile Membranes (Mini-Modules):

The sieving coefficients of myoglobin, ovalbumin and albumin in aqueous solution were tested using mini-modules comprising membranes taken out of a sterile filter (methods described above). The results are shown in Table 11.

TABLE 11

Lp value, SC of myoglobin, ovalbumin and
albumin measured in aqueous solution.

| | | Sieving coefficient in aqueous solution [%] | | | | |
|---|---|---|---|---|---|---|
| | Lp [10$^{-04}$*cm/ | Myoglobin, 17 kD | | Ovalbumin, 44 kD | | Albumin, 66 kD |
| Membrane | bar*s] | 15' | 60' | 15' | 60' | 15' |
| Comparative Example 7 | 61.3 | 64.9 | 52.4 | <21.1* | <21.2* | 0.7* |

*below detection limit

Comparative Example 8

Membranes were cut out of a commercially available Hospal Nephral® AN69ST (Gambro Industries, 69330 Meyzieu, France) filter after rinsing the blood compartment of the filter for 1 hour by recirculation of 1 liter of glycerol solution (60 w/w. %) at 50 to 100 ml/min whilst the dialysate compartment was closed (to avoid ultrafiltration) and subsequent purging of the blood compartment with air for 20 minutes. Mini-modules comprising 351 fibres were prepared ($A_{eff}$=360 cm$^2$) according to the standard operation procedure. The membranes had an inner diameter of 192 μm and a width of 38 μm.

Sterile Membranes (Mini-Modules):

The sieving coefficients of myoglobin, ovalbumin and albumin in aqueous solution were tested using mini-modules comprising membranes taken out of a sterile filter (methods described above). The results are shown in Table 12.

TABLE 12

Lp value, SC of myoglobin, ovalbumin and
albumin measured in aqueous solution.

| | | Sieving coefficient in aqueous solution [%] | | | | |
|---|---|---|---|---|---|---|
| | Lp [10$^{-04}$*cm/ | Myoglobin, 17 kD | | Ovalbumin, 44 kD | | Albumin, 66 kD |
| Membrane | bar*s] | 15' | 60' | 15' | 60' | 15' |
| Comparative Example 8 | 5.6 | 61.0 | 65.6 | <19.9* | <19.3* | 9.4* |

*below detection limit

Table 13 shows the diffusive permeabilities of chloride, vitamin B12 and albumin measured in aqueous solution on unsterile hand bundles (n=200) as described above, for Comparative examples 1 and 2 and Examples 1-4.

TABLE 13

Diffusive permeabilities of chloride, vitamin
B12 and albumin measured in aqueous solution.

| | | Permeability | | |
|---|---|---|---|---|
| Example | Lp [10$^{-04}$*cm/bar*s] | Chloride [10$^{-4}$ cm/s] | Vitamin B12 [10$^{-4}$ cm/s] | Albumin [10$^{-4}$ cm/s] |
| Comparative Example 1 | 79.4 | 17.9 | 4.2 | 0.1 |
| Comparative Example 2 | 432.7 | 16.4 | 4.5 | 0.7 |
| Example 1 | 86.9 | 18.5 | 4.5 | 0.0 |

TABLE 13-continued

Diffusive permeabilities of chloride, vitamin
B12 and albumin measured in aqueous solution.

| | | Permeability | | |
|---|---|---|---|---|
| Example | Lp [10$^{-04}$*cm/bar*s] | Chloride [10$^{-4}$ cm/s] | Vitamin B12 [10$^{-4}$ cm/s] | Albumin [10$^{-4}$ cm/s] |
| Example 2 | 79.2 | 18.7 | 4.5 | 0.0 |
| Example 3 | 102.8 | 18.7 | 4.4 | 0.1 |
| Example 4 | 155.5 | 18.3 | 4.6 | 0.2 |

Figure 6:
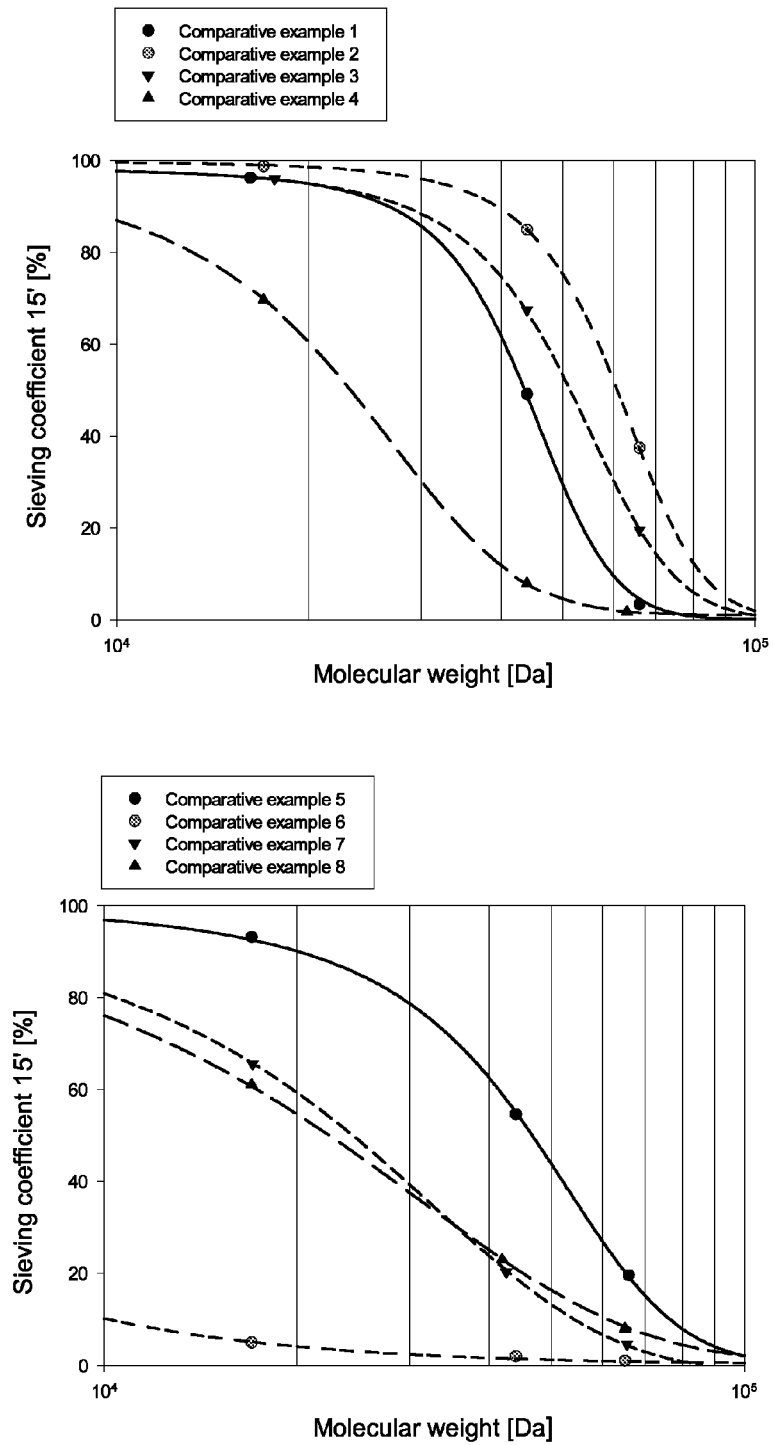
FIG. 6 shows the sieving profiles of the membranes of Comparative examples 1-4 (top) and 5-8 (bottom).

FIG. 6 shows the sieving profiles of the membranes of Comparative examples 1-4 (top) and 5-8 (bottom) created by the measured sieving coefficients after 15' in aqueous solution of myoglobin, ovalbumin and albumin, assuming that the sieving coefficient for a molecule of MW 100 Da is 100% and the sieving coefficient of a molecule of MW 1,000 kDa is 0%.

Table 14 summarizes the values of the difference of the sieving coefficient for ovalbumin (MW=44 kDa) and the sieving coefficient for albumin (MW=66 kDa) in aqueous solution for the membranes of Examples 1-4 and Comparative Examples 1-8.

TABLE 14

Difference of the sieving coefficients for
ovalbumin and albumin in aqueous solution.

| Membrane | ($SC_{Ov} - SC_{Alb}$) [%] |
|---|---|
| Example 1 | 59.7 |
| Example 2 | 56.7 |
| Example 3 | 53.1 |
| Example 4 | 55.7 |
| Comparative example 1 | 45.7 |
| Comparative example 2 | 47.5 |
| Comparative example 3 | 48.0 |
| Comparative example 4 | 5.1 |
| Comparative example 5 | 35.0 |
| Comparative example 6 | 1.8 |
| Comparative example 7 | 20.4 |
| Comparative example 8 | 10.5 |

The invention claimed is:

1. A permselective asymmetric hollow fiber membrane having a difference in sieving coefficient of the membrane for ovalbumin in aqueous solution and sieving coefficient of the membrane for albumin in aqueous solution of at least 50%, the membrane made by
    a) dissolving at least one hydrophobic polymer selected from the group consisting of polysulfones, polyethersulfones, polyamides and polyacrylonitriles, and at least one hydrophilic polymer in at least one solvent to form a polymer solution;
    b) extruding said polymer solution through an outer ring slit of a nozzle with two concentric openings;
    c) extruding a center fluid through the inner opening of the nozzle; and thereafter
    d) washing the membrane obtained;
    e) treating said membrane with a salt solution containing from 0.5 wt.-% to 12 wt.-% of a physiologically tolerable salt and no physiologically intolerable salts subsequently to washing; and thereafter
    f) drying said membrane and, optionally, sterilizing said membrane by steam treatment.

2. The membrane of claim 1, wherein the hydrophilic polymer comprises polyvinylpyrrolidone.

3. A process for preparing a permselective asymmetric hollow fiber membrane, comprising
   a) dissolving at least one hydrophobic polymer selected from the group consisting of polysulfones, polyethersulfones, polyamides and polyacrylonitriles; and at least one hydrophilic polymer in at least one solvent to form a polymer solution;
   b) extruding said polymer solution through an outer ring slit of a nozzle with two concentric openings;
   c) extruding a center fluid through the inner opening of the nozzle; and thereafter
   d) washing the membrane obtained;
   e) treating said membrane with a salt solution containing from 0.5 wt.-% to 12 wt.-% of a physiologically tolerable salt and no physiologically intolerable salts subsequently to washing; and thereafter
   f) drying said membrane and, optionally, sterilizing said membrane by steam treatment.

4. The process of claim 3 wherein the salt is sodium chloride.

5. The process of claim 3, wherein the hydrophilic polymer comprises polyvinylpyrrolidone.

6. A diffusion and/or filtration device comprising a membrane prepared by
   a) dissolving at least one hydrophobic polymer selected from the group consisting of polysulfones, polyethersulfones, polyamides and polyacrylonitriles; and at least one hydrophilic polymer in at least one solvent to form a polymer solution;
   b) extruding said polymer solution through an outer ring slit of a nozzle with two concentric openings;
   c) extruding a center fluid through the inner opening of the nozzle; and thereafter
   d) washing the membrane obtained;
   e) treating said membrane with a salt solution containing from 0.5 wt.-% to 12 wt.-% of a physiologically tolerable salt and no physiologically intolerable salts subsequently to washing; and thereafter
   f) drying said membrane and, optionally, sterilizing said membrane by steam treatment.

7. A method for at least one of hemodialysis, hemodiafiltration, and hemofiltration of blood, the method comprising preparing a membrane by
   a) dissolving at least one hydrophobic polymer selected from the group consisting of polysulfones, polyethersulfones, polyamides and polyacrylonitriles; and at least one hydrophilic polymer in at least one solvent to form a polymer solution;
   b) extruding said polymer solution through an outer ring slit of a nozzle with two concentric openings;
   c) extruding a center fluid through the inner opening of the nozzle; and thereafter
   d) washing the membrane obtained;
   e) treating said membrane with a salt solution containing from 0.5 wt.-% to 12 wt.-% of a physiologically tolerable salt and no physiologically intolerable salts subsequently to washing; and thereafter
   f) drying said membrane and, optionally, sterilizing said membrane by steam treatment, and
   performing the at least one of hemodialysis, hemofiltration and hemodiafiltration of blood using said membrane.

8. A method for at least one of bioprocessing; plasma fractionation; and the preparation of protein solutions, the method comprising preparing a membrane by
   a) dissolving at least one hydrophobic polymer selected from the group consisting of polysulfones, polyethersulfones, polyamides and polyacrylonitriles; and at least one hydrophilic polymer in at least one solvent to form a polymer solution;
   b) extruding said polymer solution through an outer ring slit of a nozzle with two concentric openings;
   c) extruding a center fluid through the inner opening of the nozzle; and thereafter
   d) washing the membrane obtained;
   e) treating said membrane with a salt solution containing from 0.5 wt.-% to 12 wt.-% of a physiologically tolerable salt and no physiologically intolerable salts subsequently to washing; and thereafter
   f) drying said membrane and, optionally, sterilizing said membrane by steam treatment, and
   at least one of treating a substance to be bioprocessed, fractionated and prepared into a protein solution using said membrane.

9. The device of claim 6 wherein the salt is sodium chloride.

10. The membrane of claim 1 wherein the salt is sodium chloride.

11. The method of claim 7 wherein the salt is sodium chloride.

12. The method of claim 8 wherein the salt is sodium chloride.

13. The device of claim 6, wherein the hydrophilic polymer comprises polyvinylpyrrolidone.

14. The method of claim 7, wherein the hydrophilic polymer comprises polyvinylpyrrolidone.

15. The method of claim 8, wherein the hydrophilic polymer comprises polyvinylpyrrolidone.

* * * * *